(12) United States Patent
Morris et al.

(10) Patent No.: US 7,851,147 B2
(45) Date of Patent: Dec. 14, 2010

(54) METHOD OF DETERMINING FATTY ACID COMPOSITION OF MILK

(75) Inventors: Christopher Anthony Morris, Hamilton (NZ); Michael Lewis Tate, Dunedin (NZ)

(73) Assignee: A2 Corporation Limited, Auckland (NZ)

( * ) Notice: Subject to any disclaimer, the term of this patent is extended or adjusted under 35 U.S.C. 154(b) by 1171 days.

(21) Appl. No.: 10/519,624

(22) PCT Filed: Jul. 3, 2003

(86) PCT No.: PCT/NZ03/00140

§ 371 (c)(1), (2), (4) Date: Aug. 15, 2005

(87) PCT Pub. No.: WO2004/004450

PCT Pub. Date: Jan. 15, 2004

(65) Prior Publication Data

US 2006/0094011 A1      May 4, 2006

(30) Foreign Application Priority Data

Jul. 3, 2002     (NZ) ...................... 520016

(51) Int. Cl.
*C12Q 1/66* (2006.01)
(52) U.S. Cl. ......................................... 435/6
(58) Field of Classification Search ........................ None
See application file for complete search history.

(56) References Cited

U.S. PATENT DOCUMENTS 6,451,368 B1     9/2002 Elliott et al.
6,570,060 B2 *   5/2003 McLachlan .................... 800/8
7,094,949 B2 *   8/2006 McLachlan ................... 800/22
7,157,616 B2 *   1/2007 Elliott et al. .................. 800/15

FOREIGN PATENT DOCUMENTS

| WO | WO 96/14577 | * | 5/1996 |
| WO | WO 96/36239 | | 11/1996 |
| WO | WO 02/19832 A1 | * | 3/2002 |

OTHER PUBLICATIONS

Bovenhuis, H. et al., "Associations Between Milk Protein Polymorphisms and Milk Production Traits", 1992 J Dairy Sci 75:2549-2559.
Ikonen, T. et al., "Associations Between Milk Protein Polymorphism and First Lactation Milk Production Traits in Finnish Ayrshire Cows", 1999 J Dairy Sci 82:1026-1033.
Laugesen, M. et al., "Ischaemic heart disease, Type 1 diabetes, and cow milk A1 β-casein", The New Zealand Medical Journal, vol. 116 No. 1168 ISSN 1175 8716 24 Jan. 2003 pp. 1-19.
McLachlan, C.N.S., "β-casein $A^1$, ischaemic heart disease mortality, and other illnesses", Medical Hypotheses (2001) 56(2), 262-272.
Ojala, M. et al., "Effects of Milk Protein Genotypes on the Variation for Milk Production Traits of Holstein and Jersey Cows in California", 1997 J Dairy Sci 80:1776-1785.
AS Truswell, "Review—The A2 milk case: a critical review", European Journal of Clinical Nutrition (2005), 59, pp. 623-631.

* cited by examiner

*Primary Examiner*—Juliet C Switzer
(74) *Attorney, Agent, or Firm*—Young & Thompson

(57) ABSTRACT

A method of reducing the level of saturated fatty acids relative to the level of unsaturated fatty acids in milk. In particular, the genotyping and/or phenotyping of bovine cows on the basis of the amino acid residue located at position 67 of beta-casein produced in their milk. The invention is based on the finding that there is a correlation between the ratio of saturated to unsaturated fatty acids in milk and the beta-casein variants in milk.

7 Claims, No Drawings

US 7,851,147 B2

METHOD OF DETERMINING FATTY ACID COMPOSITION OF MILK

TECHNICAL FIELD

This invention relates to a method for reducing the level of saturated fatty acids relative to the level of unsaturated fatty acids in milk. In particular, the invention relates to the genotyping and/or phenotyping of bovine cows on the basis of the amino acid residue located at position 67 of β-casein produced in their milk.

BACKGROUND

Dietary saturated fatty acids intake is known to be a major risk factor in heart disease in humans, particularly in countries where the population is well-nourished. Animal products, such as dairy products (especially milk), are major contributors to the dietary intake of humans. It is generally accepted that the level of saturated fatty acids found in milk, particularly those with a chain length of less that 18 carbon atoms, is a risk factor in coronary heart disease. In contrast, unsaturated fatty acids are considered to be beneficial. Because of this, there has been a preference for the consumption of plant derived oils as opposed to animal based products.

The medical community is also concerned about the consumption of fat found in milk because of the abundance of the saturated fatty acid C:14:0, which is thought to be atherogenic. The dairy industry has in part responded with the production of "low fat" milk alternatives using chemical separation and extraction techniques.

In addition to fats, specific protein components of milk, including the $A^1$ variant of the β-casein protein, are health risk factors. There are a number of reports that the consumption of β-casein $A^1$ by humans is linked with a higher incidence of certain diseases, specifically diabetes (Elliott et al. 1999 *Diabetologia* 42:292-6; Wasmuth et al. 1999 *Diabetologia* 42 (Suppl. 1):A88 Proceedings of the Kongress der Europäischen Diabetesgesellschaft vom 28.-30.09.1999 in Brüssels/Belgium) and coronary heart disease (McLachlan, C. N., *Med. Hypotheses* 56(2):262-72, 2001).

In addition to phenotyping a cow by identifying the particular β-casein variant or variants produced in the cow's milk, it is well known that a cow can be genotyped for a specific single nucleotide polymorphism (SNP) to determine which β-casein variant or variants she will produce in her milk. A method of selecting bovine cows on the basis of this genotyping methodology to give milking herds which will produce milk free of the β-casein $A^1$ variant, and preferably solely the β-casein $A^2$ variant, is the subject of PCT/NZ96/00039 (published as WO 96/36239).

The applicant has now found that there is a correlation between the ratio of saturated to unsaturated fatty acids in milk and the β-casein variants in milk. While there are known methods of altering the fatty acid composition of animal products, these typically include chemical extraction, specific feeding and management systems, and quantitative genetic selection for levels of specific fatty acids in milk. Each method is costly and usually inefficient.

It is therefore an object of the invention to provide milk, or a product obtained from that milk, which has a reduced level of saturated fatty acids relative to unsaturated fatty acids, or to at least provide the public with a useful alternative.

STATEMENTS OF INVENTION

In a first aspect of the invention there is provided a method of reducing the level of saturated fatty acids relative to the level of unsaturated fatty acids in bovine milk by:
(a) determining which cows of a herd produce milk containing β-casein having a proline at position 67, where the herd comprises cows that produce milk containing β-casein having a proline at position 67 and cows that produce milk β-casein having a histidine at position 67, by testing genetic material of individual cows of the herd for the presence of DNA encoding β-casein having a proline residue at position 67 or by testing milk produced by individual cows of the herd (or a product produced from that milk) for the presence of β-casein having a proline at position 67;
(b) selecting cows that have DNA encoding β-casein having a proline residue at position 67 or cows that produce milk containing β-casein having a proline at position 67; and
(c) milking the selected cows to give milk having a reduced level of saturated fatty acids relative to the level of unsaturated fatty acids compared with milk obtained from the herd.

It is preferred that the β-casein having a proline at position 67 includes one or more of β-caseins $A^2$, $A^3$, D, E and F. It is also preferred that the β-casein having a histidine at position 67 includes one or more of β-caseins $A^1$, B, and C.

In a preferred embodiment of the invention the β-casein having a proline at position 67 is β-casein $A^2$ and the β-casein having a histidine at position 67 is β-casein $A^1$.

It is further preferred that, in addition to reducing the level of saturated fatty acids relative to the level of unsaturated fatty acids in the milk produced by the herd of cows, the level of short and medium chain saturated fatty acids having 6 to 14 carbon atoms in each chain (C6:0-C14:0) is also reduced.

In a further preferred embodiment of the invention, determining which cows of the herd produce milk containing β-casein having a proline at position 67 is by testing the genetic material of cows for the presence of DNA encoding β-casein having a proline residue at position 67. In an alternative embodiment, determining which cows of the herd produce milk containing β-casein having a proline at position 67 is by testing the milk produced by cows (or a product produced from that milk) for the presence of β-casein having a proline at position 67.

While the genetic material of the cow may be any tissue containing, or which contained, nucleated cells, the genetic material is preferably obtained from blood, hair, or milk.

In a second aspect of the invention there is provided milk obtained by the method of the first aspect of the invention.

In a third aspect of the invention there is provided a milk product prepared from milk obtained by the method of the first aspect of the invention.

In a fourth aspect of the invention there is provided a method of altering the proportions of saturated fatty acids and unsaturated fatty acids in a food by adding to the food an amount of β-casein having a proline at position 67.

Preferably the proportions of saturated fatty acids and unsaturated fatty acids are altered by reducing the level of saturated fatty acids in the food.

Preferably the food is milk or a milk product prepared from milk. It is also preferred that the β-casein having a proline at position 67 is added to the food by adding milk (or an extract from milk) obtained by the method of the first aspect of the invention.

DETAILED DESCRIPTION OF THE INVENTION

It is well known that the genetics of an animal has a substantial impact on production levels and product quality, and on health, environmental, and animal welfare issues. The ability to determine a phenotype of an animal by using a genetic test is a valuable tool for achieving rapid identification of animals and animal products with beneficial characteristics and for forming a group of animals having enhanced production and/or product quality. Animals can be grouped based on genetic differences that relate to animal or animal product traits that are of economic interest.

The gene (or variant of that gene) that is responsible for a particular physical trait of an animal may, in some instances, be identifiable by a single nucleotide polymorphism (SNP). An SNP is a DNA sequence at a location in an animal's genome which is different to the DNA sequence at the same location in the genome of another animal by virtue of only one nucleotide. Even a difference as small as this can mean one animal exhibits a particular physical trait whereas another animal does not.

Associations between the casein content and the fat content of milk have been identified, but these have been variable in the size and direction of the correlation. The results are therefore inconclusive. Bovenhius and Weller (Genetics; 137(10): 267-80, 1994) concluded that the associations, where they exist, are due to linkage (in a sire pedigree) or linkage disequilibrium (in a population) with a fat QTL on the same cattle chromosome (chromosome 6). The overall conclusion from published data is that the total amount of fat in milk is not related to β-casein genotype and that the effect or effects that β-casein may have on human health are not related to the volume of fat intake. However, the applicant has now identified an unexpected relationship between the genotype of the β-casein gene on cattle chromosome 6 and the fatty acid composition of cow milk.

The applicant has confirmed prior findings that milk which contains βcasein $A^1$ (A1 milk) has a similar overall percentage of fat compared with milk which is free of β-casein $A^1$ (A2 milk). Surprisingly, and contradictory to previous findings, the applicant has discovered that A1 milk has a higher percentage of saturated fatty acids and a lower percentage of unsaturated fatty acids compared to A2 milk. Also surprising was the finding that the levels of C6, C8, C10, C12 and C14 fatty acids were reduced in milk from those cows homozygous for β-casein $A^2$. This significant finding shows that milk which is substantially free of β-casein $A^1$ will also produce milk fat that has lower levels of saturated fatty acids and medium chain fatty acids (C6 to C14) and higher levels of unsaturated fatty acids. Therefore, this milk has the health benefit of the reduced risk of diseases associated with a high intake of saturated fatty acids, such as atherosclerosis, obesity, coronary heart disease, and diabetes.

Typically, a cow will produce β-caseins in its milk. However, different β-casein variants exist including $A^1, A^2, A^3$, B, C, D, E, and F. The differences between these proteins are determined by sequence variations in the β-casein gene. For example, one difference is that the $A^2, A^3$, D, E, and F variants have a proline residue at position 67 whereas the $A^1$, B, and C variants have a histidine residue at position 67. This difference is determined by substitution of the nucleotide adenine with the nucleotide cytosine at position 200 of the coding region of the β-casein gene. The β-casein variant phenotype of a cow can be determined indirectly by genotyping the SNPs that are responsible for distinguishing these variant types.

The applicant has discovered that the selection of animals on the basis of β-casein variant type or the genetic variation in the β-casein gene can identify groups of animals with significant differences in their milk fatty acid compositions. For example, milk from animals which are homozygous for the adenine nucleotide at position 200 of the coding region of the β-casein gene (A1) differs in fatty acid composition from milk from animals which are heterozygous for an adenine and cytosine nucleotide (A1/A2) at this position, which differs again from milk from animals which are homozygous for a cytosine at this position (A2).

More specifically, an adenine at position 200 of the β-casein gene increases levels of the saturated fatty acids C6:0, C8:0, C10:0, C12:0 and C14:0 and decreases unsaturated fat C18:1 by a comparable amount. On removal from consideration of the effects of herd, mob within herd, breed, age 2-8+, days in milk, methylation group, and sire, the β-casein genotype accounts for 15-20% of the variation in these specific fatty acid profiles between animals.

The presence of a histidine at position 67 of β-casein enables the enzymatic formation of β-casomorphin-7. β-Casomorphin-7 is a seven amino acid peptide that is formed only from β-caseins $A^1$, B and C. Casomorphin peptides are known to act as opioids. Data from Lin et al. (1998, *Peptides* 19(2):325-31) suggest that β-casomorphin-7 may modulate the intake of dietary fat. β-Casomorphins stimulate the intake of dietary fat in rats whereas enterostatin inhibits the intake. In addition, it has been found that peptides from casein hydrolysates with tyrosyl end residues (such as β-casomorphin-7) promote peroxidase-dependent oxidation of human LDLs (low density lipoproteins). Thus, the current understanding of β-casein $A^1$, in terms of its relationship to factors that are detrimental to human health, is related to the action of casein, and peptides derived from it, on the fat metabolism of the consumer and not related to differences in the fat composition of milk from animals of different β-casein genotype.

It is unlikely that the mechanism whereby β-casein affects the fatty acid composition of milk is due to a linked gene. This is because of the size and consistency of the effect observed across sires. Without placing any limitation on the invention, it is speculated that the discovery is related to a direct effect of β-casein on the biosynthesis of lipids in mammary tissue. Alternatively, the discovery may be a direct result of the interactions of caseins with lipids in milk. If the latter is correct, it may be possible to alter the fatty acid profile of a product. Thus, the addition of β-casein obtained from animals of selected casein variant type (for example, free of β-casein $A^1$) to a product under defined processing conditions may beneficially alter the fatty acid profile of the product.

The test for β-casein can be used to select animals to include in a herd for milking or can be used to select animals to be used as sires, dams, or tissue donors for artificial breeding or cloning to breed subsequent generations of animals to be included in a herd for milking. In this way, herds of milking cows can be formed which produce milk where the β-casein $A^1$ protein is absent (or where the only β-casein present is β-casein $A^2$) in the protein fraction of the milk, and having reduced levels of specific saturated fatty acids and increased levels of a specific unsaturated fatty acids in the fat fraction of the milk. A method of selecting bovine cows on the basis of such genotyping to form milking herds which will produce milk free of the β-casein $A^1$ variant, and preferably solely the β-casein $A^2$ variant, is the subject of PCT/NZ96/00039 (published as WO 96/36239).

An additional feature of the invention is that once animals with a particular genotype have been selected and milk is produced from them, the origin of the milk, or other products, such as milk powder and processed milk products, can be verified as being produced from the selected animals. This is achieved by determining the fatty acid composition of such a milk product. Consumers can therefore be confident that the milk is indeed from animals of the desired genotype.

The benefits of the milk of this invention are considerable:
(1) the absence of β-casein $A^1$ protein and the presence of only β-casein $A^2$ produces a lower risk of coronary heart disease and Type1 diabetes
(2) replacing saturated fat with unsaturated fat produces a lower risk of coronary heart disease, obesity and other diseases
(3) the consumption of C14:0, which is thought to be atherogenic, is reduced.

The mechanism by which casein effects the fatty acid composition of milk is unclear but it is possible that it is mediated though the formation of casomorphin peptides from casein. There may be a mechanistic relationship between this and the effect of the consumption of β-casein $A^1$ by humans. However, the direct effect of casein genotype on the fatty acid profile of milk has quite separate utility from the direct effects of casein and casein metabolites on the metabolism of the consumer. There may also be a direct effect, whereby β-caseins (or particular variants) can directly modify the fatty acid composition of milk.

EXAMPLES

DNA was extracted and the fatty acid compositions determined from milk from 1114 progeny derived from six sires which were heterozygous A/C at nucleotide 200 of the β-casein gene.

DNA was extracted from the milk in the following way. Milk was mixed thoroughly by inversion and 1.0 ml was pipetted into a 1.5 ml microcentrifuge tube. The tubes were centrifuged at 8,000 rpm for 10 minutes and a 100 µl aliquot of supernatant (containing crude DNA) pipetted from each sample into a new 1.5 ml tube. The crude DNA extract was stored frozen at −20° C. and 1-5 µl was used, without further purification, for genotyping.

Genotyping methods used were have been described previously in detail in PCT/NZ96/00039 (published as WO 96/36239).

The samples for fatty acid analysis were centrifuged at 15,000 rpm for 15 minutes. An aliquot of the upper layer of lipid was removed from each sample. This lipid sample was heated to 60.0° C. and the melted lipid removed, and stored frozen. The samples were subsequently methylated and analysed by gas chromatography. The peak areas on chromatographs were integrated to quantify the levels each fatty acid. The identity of each fatty acid was determined by comparing the retention time of each peak with a known standard.

Of the samples analysed, animals either tested CC (A2), AC (A1/A2) or AA (A1) at position 200. The differences between genotypes were compared using generalised linear model analysis where the raw data was adjusted for other factors which might affect fatty acid composition. Pre-adjustments were made for: Herd, Mob within Herd, Breed, Age 2-8+, Days in Milk, and Methylation Group within Herd. Finally, Sire, Genotype, and Sire by Genotype interaction were fitted.

The results from this study are given in Table 1 and show that the A2 genotype had a significant effect on fatty acid composition. The levels of statistical significance varied between individual fatty acids (*=$p<0.05$, =$p<0.1$ *=$p<0.001$). Compared to A1, milk from animals with the A2 genotype had a significantly higher percentage of long chain unsaturated fatty acids (C18:1) and a lower percentage of saturated medium chain fatty acids in the range (C6:0-C14:0); whereas A1/A2 individuals were intermediate for these values.

As a percentage of the total C18:1, A2-derived milk had about 3% more C18:1 than A1-derived milk. C18:1 makes up about 15% of milk fat so the overall effect as a proportion of total milk fat was about half a percent more C18:1. The reduction in the percentage of saturated fatty acids was similar to the increase in unsaturated fatty acid. With the effects of herd, mob within herd, breed, age 2-8+, days in milk, methylation group and sire removed by the model, the β-casein genotype accounted for 15-20% of the variation in these specific fatty acid compositions between the animals.

TABLE 1

Summary of β-casein genotype analyses for % fatty acids in milk fat
Residuals for fatty acid traits (measured as % of total fatty acids) obtained from runs
including all animals in the Ruakura Genetics trial. Pre-adjustments were made for:
Herd, Mob within Herd, Breed, Age 2-8+, Days in Milk, Methylation Group within Herd

|  | C4:0 | C6:0 | C8:0 | C10:0 | C12:0 | C14:0 |
|---|---|---|---|---|---|---|
| n = 3760 | | | | | | |
| mean(%) | 2.67 | 2.24 | 1.56 | 3.79 | 4.31 | 12.63 |
| rsd(%) | 0.29 | 0.19 | 0.12 | 0.42 | 0.52 | 0.81 |
| adjR$^2$ | 0.44 | 0.48 | 0.47 | 0.40 | 0.40 | 0.24 |
| Model: Sire, β-casein genotype (A1; A1A2; A2), genotype × sire interaction. Traits are standardised residuals. | | | | | | |
| n = 1114 | | | | | | |
| Sire | ** | * | ** | *** | *** | *** |
| Genotype | ns | * | ** | ** | * | ** |
| Genotype × sire | ns | ns | + | ns | ns | ns |
| Contrast A2-A1 | −0.03 ± 0.10 | −0.25 ± 0.09 | −0.29 ± 0.10 | −0.26 ± 0.09 | −0.21 ± 0.10 | −0.24 ± 0.10 |
|  | (ns) | () | () | (**) | (*) | (*) |

TABLE 1-continued

Summary of β-casein genotype analyses for % fatty acids in milk fat
Residuals for fatty acid traits (measured as % of total fatty acids) obtained from runs
including all animals in the Ruakura Genetics trial. Pre-adjustments were made for:
Herd, Mob within Herd, Breed, Age 2-8+, Days in Milk, Methylation Group within Herd

| | | | | | | |
|---|---|---|---|---|---|---|
| Contrast A2-A1A2 | −0.13 ± 0.09 (ns) | −0.16 ± 0.09 (+) | −0.11 ± 0.09 (ns) | −0.06 ± 0.09 (ns) | −0.05 ± 0.09 (ns) | −0.03 ± 0.09 (ns) |
| Contrast A1-A1A2 | −0.10 ± 0.08 (ns) | 0.09 ± 0.07 (ns) | 0.18 ± 0.07 (*) | 0.20 ± 0.07 (**) | 0.16 ± 0.07 (*) | 0.20 ± 0.07 (**) |

| C15:0 | C16:0 | C16:1 | C18:0 | C18:1 | C18:1 trans | C18:2 | CLA |
|---|---|---|---|---|---|---|---|
| 1.36 | 30.48 | 1.33 | 9.45 | 15.69 | 3.48 | 1.36 | 0.84 |
| 0.16 | 2.71 | 0.29 | 1.37 | 1.85 | 0.87 | 0.20 | 0.27 |
| 0.26 | 0.22 | 0.26 | 0.28 | 0.27 | 0.34 | 0.60 | 0.36 |

Model: Sire, β-casein genotype (A1; A1A2; A2), genotype × sire interaction. Traits are standardised residuals.

| | | | | | | | |
|---|---|---|---|---|---|---|---|
| *** | *** | *** | *** | *** | *** | *** | *** |
| ns | ns | ns | ns | * | ns | ns | ns |
| ns | ns | ns | ns | ns | ns | ns | ns |
| 0.01 ± 0.10 (ns) | −0.07 ± 0.10 (ns) | 0.04 ± 0.10 (ns) | 0.01 ± 0.09 (ns) | 0.26 ± 0.10 (**) | 0.08 ± 0.10 (ns) | 0.09 ± 0.11 (ns) | 0.16 ± 0.10 (ns) |
| −0.01 ± 0.09 (ns) | −0.09 ± 0.09 (ns) | −0.02 ± 0.09 (ns) | 0.09 ± 0.09 (ns) | 0.12 ± 0.09 (ns) | 0.07 ± 0.10 (ns) | 0.001 ± 0.10 (ns) | 0.10 ± 0.09 (ns) |
| −0.02 ± 0.08 (ns) | −0.02 ± 0.08 (ns) | −0.06 ± 0.08 (ns) | 0.08 ± 0.07 (ns) | −0.14 ± 0.07 (+) | −0.003 ± 0.08 (ns) | −0.09 ± 0.08 (ns) | −0.06 ± 0.08 (ns) |

Although the invention has been described by way of example, it should be appreciated that variations and modifications may be made without departing from the scope of the invention. Furthermore, where known equivalents exist to specific features, such equivalents are incorporated as if specifically referred in this specification.

INDUSTRIAL APPLICABILITY

Milk having a low level of saturated fatty acids compared to unsaturated fatty acids is useful for the avoidance of certain diseases and disorders. Dietary fatty acid intake is a major risk factor in heart disease and much of that dietary fatty acid intake is from the consumption of milk and milk products. The ability to obtain milk low in saturated fatty acids relative to unsaturated fatty acids by milking only those cows that have been genotyped or phenotyped on the basis of their ability to produce β-casein variants having proline, rather than histidine, at position 67 represents a useful method of producing milk beneficial to human health.

The invention claimed is:

1. A method of determining relative levels of saturated fatty acids and unsaturated fatty acids in bovine milk obtained from one or more cows:
   (a) testing genetic material of the one or more cows for the presence of DNA encoding β-casein having a proline residue at position 67 or DNA encoding β-casein having a histidine residue at position 67;
   (b) identifying whether a cow or cows (i) will likely have a lower percentage of saturated fatty acids and a higher percentage of unsaturated fatty acids based on being homozygous for DNA encoding β-casein having a proline residue at position 67 or (ii) will likely have a higher percentage of saturated fatty acids and a lower percentage of unsaturated fatty acids based on being homozygous for the DNA encoding β-casein having a histidine residue at position 67 for which genetic material was tested in (a); and
   (c) obtaining milk from at least one of the one or more cows after step (b).

2. The method as claimed in claim 1, wherein the β-casein having a proline at position 67 includes one or more of β-caseins A2, A3, D, E and F.

3. The method as claimed in claim 2, wherein the β-casein having a proline at position 67 is β-casein A2.

4. The method as claimed in claim 1, wherein the β-casein having a histidine at position 67 includes one or more of β-caseins A1, B, and C.

5. The method as claimed in claim 4, wherein, the β-casein having a histidine at position 67 is β-casein A1.

6. The method as claimed in claim 1, wherein the genetic material of the cows may be any tissue containing, or which contained, nucleated cells.

7. The method as claimed in claim 6, wherein the genetic material is obtained from blood, hair, or milk.

* * * * *